US012770728B2

(12) United States Patent
Juster

(10) Patent No.: US 12,770,728 B2
(45) **Date of Patent: *Oct. 20, 2026**

(54) PRESENTING THERAPY EVENTS ON A CONTINUOUS, TIME-BASED DATA FEED

(71) Applicant: Tandem Diabetes Care, Inc., San Diego, CA (US)

(72) Inventor: Josh Juster, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 18/936,921

(22) Filed: Nov. 4, 2024

(65) Prior Publication Data

US 2025/0062002 A1 Feb. 20, 2025

Related U.S. Application Data

(63) Continuation of application No. 17/517,885, filed on Nov. 3, 2021, now Pat. No. 12,136,479.

(60) Provisional application No. 63/109,565, filed on Nov. 4, 2020.

(51) Int. Cl.
*G16H 20/40* (2018.01)
*G16H 40/63* (2018.01)

(52) U.S. Cl.
CPC ............. *G16H 20/40* (2018.01); *G16H 40/63* (2018.01)

(58) Field of Classification Search
CPC ....................................................... G16H 20/40
See application file for complete search history.

(56) References Cited

U.S. PATENT DOCUMENTS

2005/0267780 A1* 12/2005 Ray ........................ G16H 15/00 705/2
2011/0193704 A1* 8/2011 Harper ................... A61B 5/743 340/505
2014/0068487 A1* 3/2014 Steiger ................. A61B 5/7275 715/771

(Continued)

OTHER PUBLICATIONS

"Display of Glucose Distributions by Date, Time of Day, and Day of Week: New and Improved Methods"; David Rodbard, M.D.; Journal of Diabetes Science and Technology; Nov. 2009 (Year: 2009).*

(Continued)

*Primary Examiner* — John A Pauls
(74) *Attorney, Agent, or Firm* — Straylight LLP

(57) ABSTRACT

Disclosed herein are methods for presenting therapy events on a continuous, time-based data feed. An algorithm for arranging data on the feed can position icons on the feed with information regarding therapy events at a time each event occurred without blocking or interfering with the data feed, including when the data feed is scrolled, zoomed, or otherwise repositioned. The algorithm can include clustering, buffering and affinity components. The clustering component can combine different events occurring at the same time into a single event and keep those events visually together on the data feed. The buffering component can provide a buffer around each event so there is no overlapping of depicted events. The affinity component provides an affinity for placing events as closed to a CGM trend line on the data feed as possible in view of the positioning of other events.

20 Claims, 3 Drawing Sheets

(56) References Cited

U.S. PATENT DOCUMENTS

| | | | | |
|---|---|---|---|---|
| 2014/0181083 | A1* | 6/2014 | Macho | G06F 16/252 707/769 |
| 2015/0379097 | A1* | 12/2015 | Robertson | G06F 3/0482 707/725 |
| 2016/0103604 | A1* | 4/2016 | Johnson | G06F 3/0488 715/772 |
| 2017/0061078 | A1* | 3/2017 | Natsume | G16H 10/40 |

OTHER PUBLICATIONS

Rodbard, Display of Glucose Distributions by Date, Time of Day, and Day of Week: New and Improved Methods, Journal of Diabetes Science and Technology, Nov. 2009.

* cited by examiner

300

PRESENTING THERAPY EVENTS ON A CONTINUOUS, TIME-BASED DATA FEED

RELATED APPLICATIONS

This Application is a continuation of U.S. patent application Ser. No. 17/517,885 (filed Nov. 3, 2021), which claims the benefit of U.S. Provisional App. No. 63/109,565 (filed Nov. 4, 2020). Both of these applications are hereby incorporated by reference in their entirety.

TECHNICAL FIELD

The present disclosure relates, generally, to diabetes therapy and, more particularly, to presentation of therapy data for diabetes therapy on a user interface.

BACKGROUND

People with diabetes can treat the disease in a number of different ways, including insulin pumps, insulin pens, and regular injections with a syringe. Regardless of the method of treatment, it is important for the user to be able to track and review data relating to therapy in order to aid the user in better managing the user's diabetes.

A number of different data management software programs, mobile applications, etc. have therefore been developed that enable a user to review therapy data. Given that a variety of events can impact treatment and diabetes therapy, it can be difficult to present all relevant data over a given time period on a single screen without obscuring other data and to adjust the display of data when a different time period is displayed. For example, and in particular for smaller screens on portable pumps and/or remote control devices such as smartphones, data may overlap or be otherwise difficult to read or interpret.

SUMMARY

Disclosed herein are methods for presenting therapy events on a continuous, time-based data feed. An algorithm for arranging data on the feed can position icons on the feed with information regarding therapy events at a time each event occurred without blocking or interfering with the data feed, including when the data feed is scrolled, zoomed, or otherwise repositioned. The algorithm can include clustering, buffering, and affinity components. The clustering component can combine different events occurring at the same time into a single event and keep those events visually together on the data feed. The buffering component can provide a buffer around each event so there is no overlapping of depicted events. The affinity component provides an affinity for placing events as closed to a CGM trend line on the data feed as possible in view of the positioning of other events. The system and methods disclosed herein therefore provide an improved user interface that enables a user to easily view and interpret relevant data over a displayed time period, even on a relatively small screen, including when new data is received or when the display is otherwise modified.

In an embodiment, a method for presenting diabetes therapy events on a continuous, time-based data feed can include receiving glucose level data of a user, receiving data relating to a plurality of events pertaining to diabetes therapy, and presenting a continuous, time-based data feed on a display over a predetermined time frame. A glucose level trend line can be displayed on the continuous, time-based data feed depicting the glucose level data of the user over the predetermined time frame. Event icons pertaining to the plurality of events occurring during the predetermined time frame can be arranged around the glucose level trend line on the continuous, time-based data feed with the event icons arranged such that each event icon is positioned on the continuous, time-based data feed at a time when the event corresponding to the event icon occurred and each event icon can be displayed without obscuring the glucose level trend line or any of the other event icons. The continuous, time-based data feed can be continually updated over time as updated glucose level data is received and information pertaining to additional events is received.

In an embodiment, a method for presenting diabetes therapy events on a continuous, time-based data feed can include receiving glucose level data of a user, receiving data relating to a plurality of events pertaining to diabetes therapy and presenting a continuous, time-based data feed on a display over a predetermined time frame. A glucose level trend line can be displayed on the continuous, time-based data feed depicting the glucose level data of the user over the predetermined time frame. A plurality of event icons relating to the plurality of events occurring during the predetermined time frame can be displayed, including clustering event icons of events occurring at the same time on the data feed at the time the events occurred, providing a buffer around each event icon to prevent the event icons from overlapping each other and arranging each event icon as close as possible to the glucose level trend line without obscuring the glucose level trend line or any of the other event icons. The continuous, time-based data feed can be continually updated over time as updated glucose level data is received and information pertaining to additional events is received.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

Figure 1:
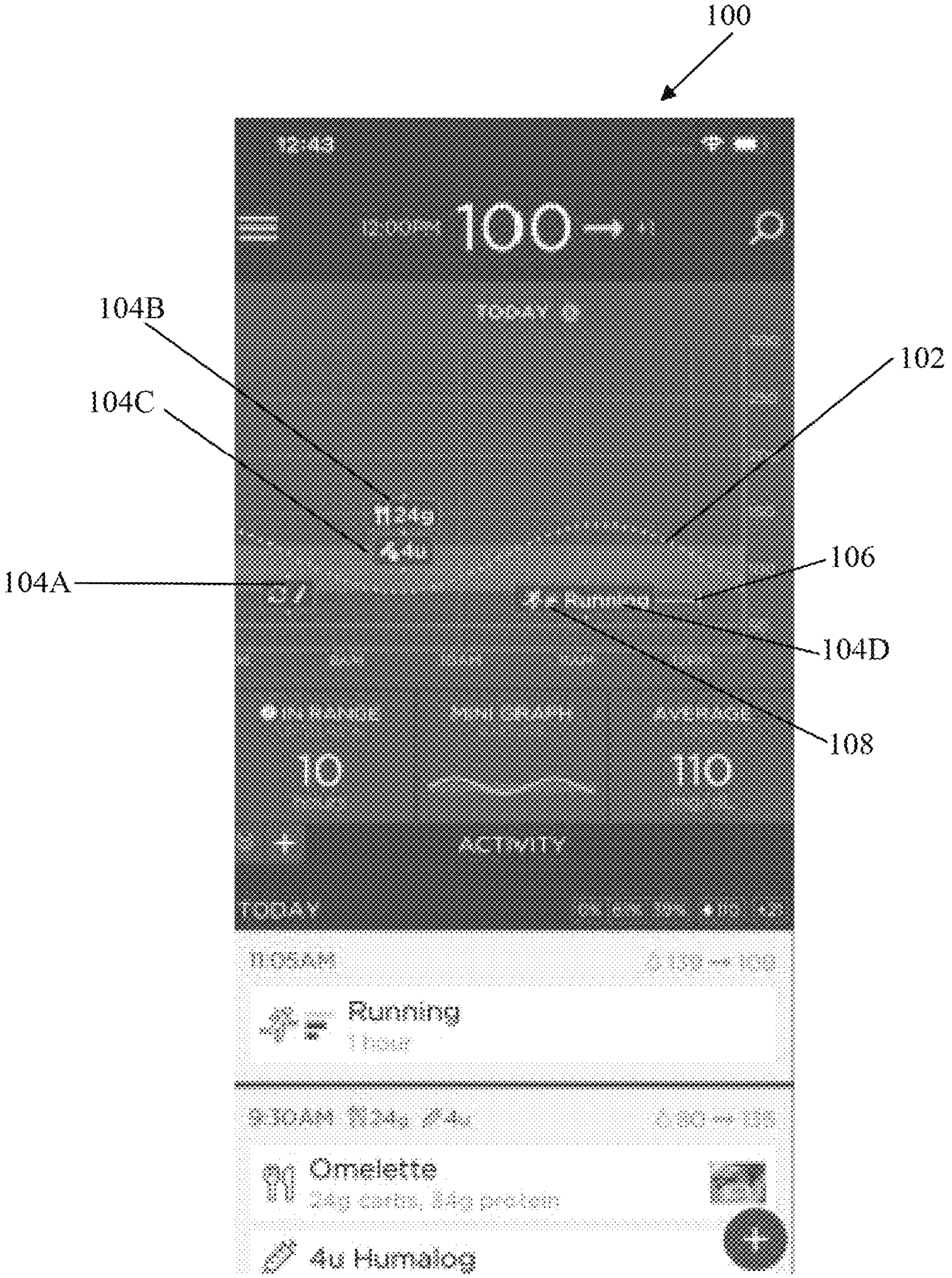
FIG. 1 depicts a continuous, time-based data feed according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Referring to FIG. 1, a continuous, time-based data feed 100 for diabetes therapy is depicted. In embodiments, the data feed can be displayed on a mobile device such as a smartphone operating a software application that receives and displays therapy data. Due to the relatively small screen size of such devices, display of multiple therapy events in a given time frame can be difficult. In other embodiments, the data feed can be displayed on any other display device, such as, for example, a tablet computer, desktop computer, or laptop. The disclosed system executes an algorithm that provides a best fit for each therapy event that occurred over the displayed time frame without covering up or otherwise obscuring the data feed or overlapping the various events. The algorithm can further reconfigure the displayed events as needed when the graph is zoomed in or out, the timeframe is changed, the graph is scrolled, shifted between portrait mode and landscape mode, etc. Diabetes therapy can be provided in any manner, including, for example, with an ambulatory infusion pump, an insulin pen, and multiple daily injections.

Data feed 100 can include a CGM trend line 102 that shows the user's glucose levels (y-axis) over a previous time period (x-axis). As additional data is received, it is added to the graph such that the graph continuously moves forward in time. In embodiments, the user can cause the system to scroll back and view the glucose levels over previous time periods, days, weeks, etc. on an updated glucose trend line over the updated time period. The user can further zoom in or zoom out on the data feed. In some embodiments, when the user zooms in or out on the data feed only the x-axis (time) and the size of the icons on the graph is modified. In such embodiments, the user is able to zoom in to enlarge the icons or out to view additional icons/time, but the scale of y-axis (glucose level) is fixed such that the CGM readings' heights do not change to enable the user to more easily interpret the data without having to adjust to a different looking CGM graph. The glucose readings can generally be measured by a continuous glucose monitor. In various embodiments, the data application can obtain the CGM data from a third party diabetes data management system, from an ambulatory infusion pump or other therapy device, and/or directly from the CGM.

Data feed 100 can also function as an activity tracker that displays various events 104A-104D related to the user's therapy and/or that have an effect on glucose levels in order to aid the user in understanding how those events impact the user's therapy. Such events can include, for example, meals, bolus deliveries, temporary basal rates, exercise, device changes, medication, manual blood glucose measurements and notes relating to therapy. For example, event 104A indicates that the user changed insulin pens around 8:30 am. Around 9:30 am, the user had a meal and delivered a bolus as indicated by the meal icon 104B depicting that 24 grams of carbohydrates were consumed and the bolus icon 104C indicating the 4 units of insulin were delivered. A running icon 104D indicates that the user exercised by going for a run from 10:30 to 11:30. The width of icons 104A-104D can be independent of an amount of time that the event takes and can instead be based on the amount of information that needs to be conveyed on the data feed about the event, but each icon is positioned on the feed at a time when the event began. For example, if fewer icons need to be displayed, the icons can be displayed larger in order for the icons to be more easily interpreted. In some embodiments, some or all icons may have a minimum width requirement regardless of how many icons will be presented based on a size needed to properly convey the information represented by the icon, with the icons positioned along the y-axis of the graph as needed to display all icons. For events that occur over an extended length of time, a timeline 106 can indicate the time over which the event occurs, including an end time. For activities such as exercise, an intensity of the exercise can also be indicated. For example, intensity indicator 108 in FIG. 1 consists of a series of horizontal bars with more bars being highlighted the higher the intensity of the exercise. In various embodiments, event icons may include a pictorial icon representing a given event, textual information or both. In some embodiments, a user can select whether event icons include textual information in additional to pictorial icons.

Information relating to therapy events can be obtained by the data application from a variety of sources. For example, a user can manually enter data associated with any event. For therapy provided by ambulatory infusion pumps, smart insulin pens or any other device capable of wireless communications, the therapy device can automatically transmit therapy data to the data application. Exercise and food information can be obtained from health management applications operating on smartphones or other devices. Exercise information could further be obtained from a fitness app or directly from an activity monitoring device, such as a smartwatch.

The event presentation algorithm that positions the various events in a given time period on the data feed can include three major components that serve to position events in an optimal way around CGM feed 102 with sufficient information/size to convey the nature of the event but without obscuring either the CGM feed or adjacent events. The three major components are clustering, buffering, and affinity. Clustering takes different events that occur at or around the same time and groups them into a single event so that those events remain visually together on the data feed. Referring to FIG. 1, the meal event 104B and the bolus event 104C have been clustered together to be aligned vertically around the time the events occurred. Buffering provides a buffer around each event to prevent events from overlapping each other. An affinity component places all items as close vertically to the CGM trend line 102 as possible in view of the positioning of other items.

These components work together to place all events in a given timeframe on the data feed and to update the data feed in real time as new data is acquired. In addition, the algorithm must take into account past events that are not currently on the data feed. For example, past events might appear if the user were to scroll back on the feed causing such events to appear along with some events that were previously displayed and the algorithm is configured to keep the previous events in the same location on the graph when the earlier data appears because constantly moving events around would make the graph more difficult to follow and less user friendly. Thus, the positioning of past events close in time with current events is considered in placing the current events in order to enable events to be presented without overlap and without moving the events if the user scrolls back to display the past events. Further, events with a timeline 106 (such as the running event 104D in FIG. 1) can appear on the feed if the timeline is in the current time period even if the event began before the displayed time period such that the event icon is not displayed. Such events can therefore be fixed to the data feed based on the end point of the timeline rather than the event icon. The algorithm therefore continually operates to place items in an optimal way around the data feed any time the feed is scrolled forward or back, zoomed in or out, or the scale of the graph is changed.

Figure 2:
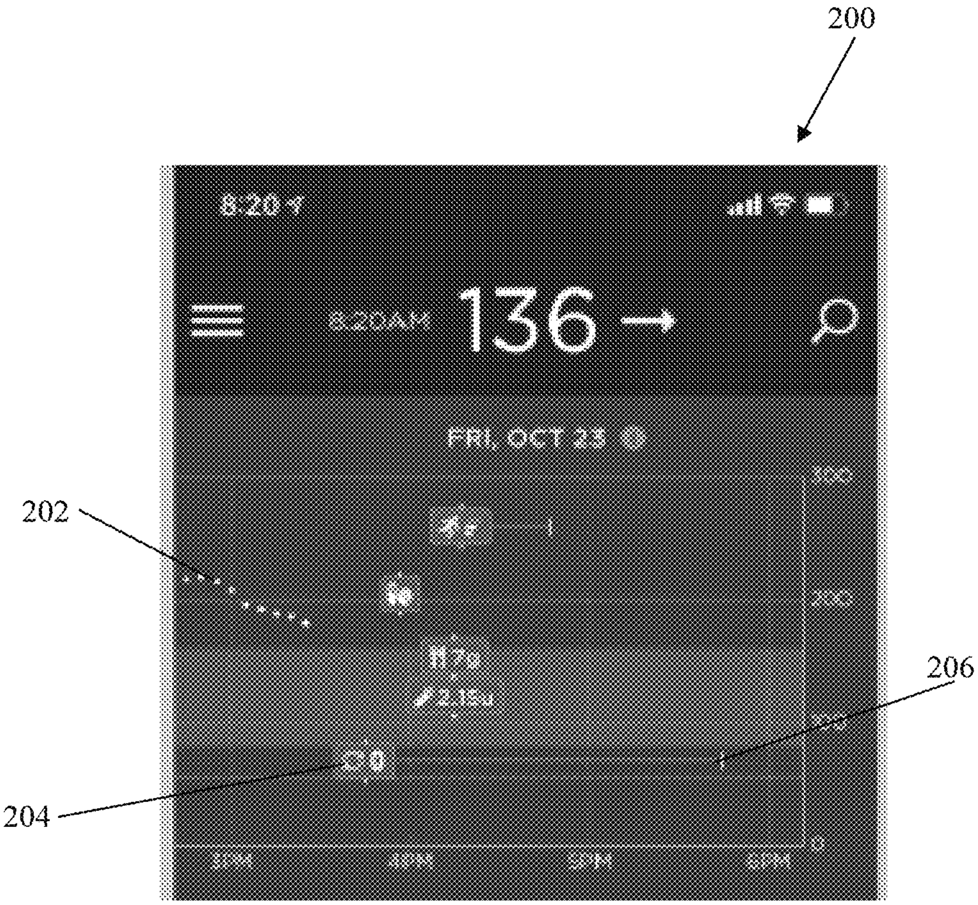
FIG. 2 depicts a continuous, time-based data feed according to an embodiment.

FIG. 2 depicts another continuous, time-based data feed 200 for diabetes therapy. In this embodiment, the CGM data feed 202 ends between 3:00 pm and 4:00 pm. This can happen for a variety of reasons including, for example, replacement of the CGM sensor, replacement of the CGM transmitter and loss of wireless connectivity with the CGM sensor. In some embodiments, the user can add an icon into the data feed that provides a visual representation as to why CGM data is missing. In FIG. 2, a replaced sensor icon 204 is displayed on the graph along with a timeframe object 206 showing a two hour warm up period for the sensor before new CGM data is received. In this manner, when a user scrolls through data the user can see why the data is missing. In addition, in some embodiments a missing data alarm that would be otherwise issued to alert the user to missing CGM data can be suspended when the user adds a device change icon to the missing portion of the graph.

Figure 3:
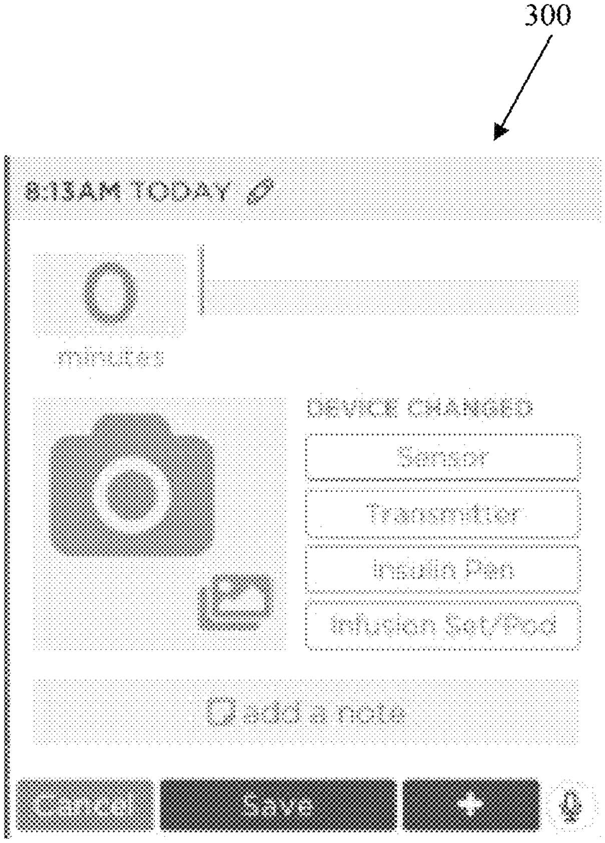
FIG. 3 depicts a changed device event log according to an embodiment.

FIG. 3 depicts a device change event log 300 that enables a user to enter a device change such as a sensor or transmitter change onto the graph by selecting an area of the graph to which to add the icon. The device change log can further indicate additional device changes that may not have a corresponding loss of CGM data such as changing an insulin pen (shown in FIG. 1) and changing an infusion set or infusion cartridge. A user can further enter a number of minutes for the device change, add a photo related to the device change, and/or enter notes relating to the device change in the device change event log 300. When the user saves the device change, it will appear on the graph at the selected location as shown in the figures. Some device change events, such as infusion set or cartridge changes, can be automatically received from a corresponding device (e.g., an infusion pump) and automatically populated onto the data feed.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable medical indication or application. Non-medical applications are also contemplated, including fitness tracking and meal logging applications.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 6,999,854; 8,133,197; 8,287,495; 8,408,421; 8,448,824; 8,573,027; 8,650,937; 8,986,523; 9,173,998; 9,180,242; 9,180,243; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10,541,987; 10,569,016; 10,736,037; 10,888,655; 10,994,077; and 11,116,901; commonly owned U.S. Patent App. Pub. Nos. 2009/0287180; 2012/0123230; 2013/0053816; 2014/0276423; 2014/0276569; 2014/0276570; 2018/0071454; 2019/0240398; 2019/0307952; 2020/0114076; 2020/0206420; 2020/0261649; 2020/0306445; 2020/0329433; 2020/0368430; 2020/0372995; 2021/0001044; 2021/0113766; and 2021/0154405; and commonly owned U.S. patent application Ser. Nos. 17/323,529; 17/368,968; and Ser. No. 17/459,129.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

What is claimed is:

1. A method for presenting events pertaining to diabetes therapy on a continuous, time-based data feed, the method comprising:

receiving glucose level data associated with a user;

receiving event data corresponding to an event that affects a glucose level of the user or relates to a diabetes therapy of the user;

displaying a continuous, time-based data feed for a predetermined time frame;

displaying a trend line on the continuous, time-based data feed, wherein the trend line depicts the glucose level data of the user for the predetermined time frame; and displaying an event icon near the trend line, wherein the event icon corresponds to the event and comprises an intensity indicator that indicates an intensity of the event.

2. The method of claim 1, further comprising:

receiving additional event data corresponding to another event that affects the glucose level of the user or relates to the diabetes therapy of the user;

displaying another event icon near the trend line, wherein the other event icon corresponds to the other event and comprises another intensity indicator that indicates an intensity of the other event.

3. The method of claim 2, wherein displaying the event icon and the other event icon comprises providing respective buffers around each of the event icon and the other event icon to prevent the event icon and the other event icon from overlapping.

4. The method of claim 2, wherein:

displaying the event icon comprises displaying the event icon (i) at a time on the continuous, time-based data feed corresponding to when the event occurred and (ii) at a location on the continuous, time-based data feed where the event icon does not obscure the trend line; and displaying the other event icon comprises displaying the other event icon (i) at another time on the continuous, time-based data feed corresponding to when the other event occurred and (ii) at another location on the continuous, time-based data feed where the other event icon does not obscure the trend line.

5. The method of claim 4, wherein displaying the event icon and the other event icon near the trend line comprises displaying each of the event icon and the other event icon as close as possible to the trend line without obscuring the trend line.

6. The method of claim 1, further comprising displaying a timeline indicator adjacent to the event icon, wherein the timeline indicator indicates a duration and end time of the event.

7. The method of claim 1, further comprising maintaining a positioning of each event icon relative to the trend line when the user scrolls in time on the continuous, time-based data feed.

8. The method of claim 1, wherein receiving the event data comprises automatically receiving the event data from an infusion pump, an insulin pen, or an activity monitoring device.

9. The method of claim 1, wherein receiving the event data comprises automatically receiving the event data from a healthcare-related application operating on a same device at which the continuous, time-based data feed is displayed.

10. The method of claim 1, wherein the event comprises a meal, a bolus delivery, a temporary basal rate, an exercise, a medication taken, or a manual blood glucose measurement.

11. A mobile device comprising:

a display;

a processor configured to:

receive glucose level data associated with a user;

receive event data corresponding to an event that affects a glucose level of the user or relates to a diabetes therapy of the user;

display, via the display, a continuous, time-based data feed for a predetermined time frame;

display, via the display, a trend line on the continuous, time-based data feed, wherein the trend line depicts the glucose level data of the user for the predetermined time frame; and display an event icon near the trend line, wherein the event icon corresponds to the event and comprises an intensity indicator that indicates an intensity of the event.

12. The mobile device of claim 11, wherein the processor is further configured to:

receive additional event data corresponding to another event that affects the glucose level of the user or relates to the diabetes therapy of the user;

display, via the display, another event icon near the trend line, wherein the other event icon corresponds to the other event and comprises another intensity indicator that indicates an intensity of the other event.

13. The mobile device of claim 12, wherein displaying the event icon and the other event icon comprises providing respective buffers around each of the event icon and the other event icon to prevent the event icon and the other event icon from overlapping.

14. The mobile device of claim 12, wherein:

displaying the event icon comprises displaying the event icon (i) at a time on the continuous, time-based data feed corresponding to when the event occurred and (ii) at a location on the continuous, time-based data feed where the event icon does not obscure the trend line; and displaying the other event icon comprises displaying the other event icon (i) at another time on the continuous, time-based data feed corresponding to when the other event occurred and (ii) at another location on the continuous, time-based data feed where the other event icon does not obscure the trend line.

15. The mobile device of claim 14, wherein displaying the event icon and the other event icon near the trend line comprises displaying each of the event icon and the other event icon as close as possible to the trend line without obscuring the trend line.

16. The mobile device of claim 11, wherein the processor is further configured to display a timeline indicator adjacent to the event icon, wherein the timeline indicator indicates a duration and end time of the event.

17. The mobile device of claim 11, wherein the processor is further configured to maintain a positioning of each event icon relative to the trend line when the user scrolls in time on the continuous, time-based data feed.

18. The mobile device of claim 11, wherein receiving the event data comprises:

automatically receiving the event data from an infusion pump, an insulin pen, or an activity monitoring device; or automatically receiving the event data from a healthcare-related application operating on a same device at which the continuous, time-based data feed is displayed.

19. The mobile device of claim 11, wherein the event comprises a meal, a bolus delivery, a temporary basal rate, an exercise, a medication taken, or a manual blood glucose measurement.

20. A non-transitory, computer-readable medium storing instructions that, when executed by a processor of a mobile device, cause the mobile device to perform operations including:

receiving glucose level data associated with a user;

receiving event data corresponding to an event that affects a glucose level of the user or relates to a diabetes therapy of the user;

displaying a continuous, time-based data feed for a predetermined time frame;

displaying a trend line on the continuous, time-based data feed, wherein the trend line depicts the glucose level data of the user for the predetermined time frame; and displaying an event icon near the trend line, wherein the event icon corresponds to the event and comprises an intensity indicator that indicates an intensity of the event.

* * * * *